United States Patent [19]
Schläpfer et al.

[11] Patent Number: 5,312,402
[45] Date of Patent: May 17, 1994

[54] CONNECTION DEVICE

[75] Inventors: Johannes F. Schläpfer, Glarus; Martin Hess, Holstein, both of Switzerland

[73] Assignee: Synthes (U.S.A.), Paoli, Pa.

[21] Appl. No.: 868,978

[22] Filed: Apr. 16, 1992

[30] Foreign Application Priority Data

Apr. 16, 1991 [CH] Switzerland .......... 01 124/91-4

[51] Int. Cl.$^5$ .............................................. A61F 5/00
[52] U.S. Cl. ........................................ 606/53; 606/61
[58] Field of Search .................... 606/60, 61, 53, 64, 606/72, 73

[56] References Cited

U.S. PATENT DOCUMENTS 5,122,131 6/1992 Tsou .................................... 606/61
5,129,899 7/1992 Small et al. ......................... 606/61

Primary Examiner—Robert A. Hafer
Assistant Examiner—Sam Rimell
Attorney, Agent, or Firm—Davis Hoxie Faithfull & Hapgood

[57] ABSTRACT

The connection device (20) for adjustable connection of a first with a second structural element (12, 13), particularly tubes or rods, for a setting device has an external component (21) with a cylindrical hole and two internal components (22) inserted into the hole so that they can be slid axially and rotatably, each of which said internal components (22) has through openings (24, 25) crossways to the axial direction of the components to hold a structural element (12, 13). By means of loading means (23, 29), designed as a nut/screw connection, the internal component (2) is pushed axially to the external component (21) and thereby grips the inserted structural elements (12, 13). A recess (26) in the internal component (22) effectuates a flexible radial deformation of the internal against the external component (22, 21), said deformation being created through the inserted structural element (12, 13), and an additional bonding of the connection device (20) is thereby achieved, which considerably improves the setting.

21 Claims, 4 Drawing Sheets

CONNECTION DEVICE

FIELD OF THE INVENTION

The invention concerns a connection device for adjustably connecting a first structural element with a second structural element. The invention is of particular use in systems for the setting of bones where the structural elements are tubes or rods used in external fixation systems.

BACKGROUND OF THE INVENTION

A known connection device for use in osteosynthetic external fixation systems comprises on the one hand two gripping jaws and a screw that goes through them, and on the other hand a loop connected with said screw, a U-shaped counterpart that envelops the loop, and a screw that goes through this counterpart and is attached to the loop. Advantageously, this connection device is attached to, for example, a Schanze entrenchment screw, by means of the gripping jaws, while a rod, for example a carbon filament rod, can be secured to the opposing segment of the connection device. The carbon filament rod is positioned approximately parallel to the broken bone to be treated and is connected via several of said connection devices with Schanze screws screwed into the bone on both sides at the fracture; the desired external setting of the bone is thereby achieved. It is very important that the connection device be very easy to handle and that a very rigid setting be achieved without excessive expenditure of force, so that in case of shocks or other outside influences the bone parts will not shift in relation to each other and so that even after the passage of time the setting will retain its rigidity. In the known connection device described, experience has shown that over an extended period of time the tension in the setting device can slacken somewhat, and leading to conditions not always optimum.

SUMMARY OF THE INVENTION

In accordance with the present invention, a connection device is formed which is of a simple design and capable of flexible handling to provide a connection that is secure and will retain its rigidity over an extended period of time.

A connection device according to the invention has an external component having a cylindrical hole and an internal cylindrical component that can be slid axially in the hole, said internal component having one or preferably two through openings, both transverse to its axis, to hold structural elements, which, when inserted, can be locked in place by sliding the internal and external components axially relative to each other by means of a loading means.

More specifically, in a device according to the invention, the internal component has at least one recess by means of which the component can be flexibly deformed when it is urged against an inserted structural element and can thereby be additionally pressed against and frictionally bonded with the external component, in addition to clamping the structural element. This meets the aforementioned requirements in an ideal manner, for with such an arrangement a bond is created between the internal component and the external component, and thus, despite the simple design and ease of use, a very effective and reliably stable connection is achieved.

Advantageously, the surfaces of the internal and external components that contact each other are equipped with structured or toothed surfaces, whereby an even greater security against twisting of these two components is achieved. The external diameter of the internal component in relation to the external component is such that it is held in the external element either rotatably and unstressed, or locked positively therewith.

The loading means can include a nut that can be screwed onto a corresponding threaded segment on the internal component, and which thereby brings the internal component into connection with the external component. However, it can also comprise a set screw that can be screwed into a threaded hole in the internal component, thereby coming into contact with a structural element inserted therein.

The through openings provided for the structural elements are designed as slots in the components. Such through openings permit the inserted structural elements a range of angular mobility.

BRIEF DESCRIPTION OF THE DRAWINGS

The invention will be further described with reference to the accompanying drawings in which.

DETAILED DESCRIPTION OF THE INVENTION

Figure 1:
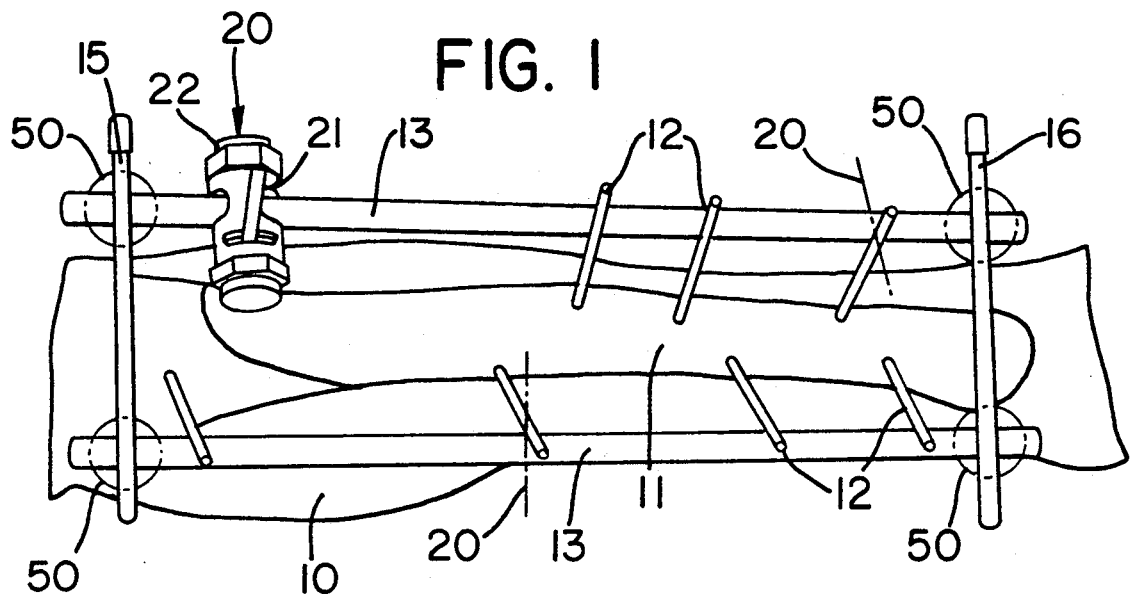
FIG. 1 is a schematic perspective view of an external fixation system using connection devices according to the invention.

Referring to FIG. 1, an osteosynthetic external fixation system device is shown applied to a bone fracture in a partially illustrated leg 10. Screwed into the bone (shinbone) 11 along its length are structural elements in the form of Schanze screws 12, positioned in two rows of four screws each, while other structural elements in the form of two carbon filament rods 13 are positioned approximately parallel to bone 11. By means of connection devices 20 according to the invention, each screw 12 is rigidly connected with the corresponding carbon filament rod 13. Additional structural elements in the form of connecting rods 15 and 16, positioned crossways at both ends of rods 13, and permanently connected with this rod 13 by means of connecting devices 50 according to the invention, give the injured bone an additional rotation stability. Theoretically, the same devices 20 used to connect the screws 12 and the rod 13 can be used to connect the rods 15, 16 instead of the connection device 50.

Each rod is shown as round, but the rods can have a rectangular or other section. The carbon filament rods are permeable to X-rays.

Figure 2:
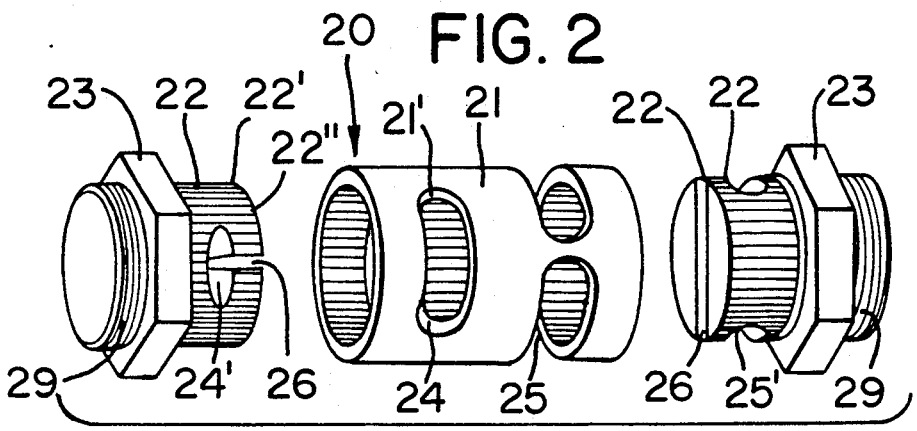
FIG. 2 is an exploded perspective view of a connection device according to the invention.

Details of the connection device 20 are shown in FIG. 2. Referring to FIG. 2, the device 20 comprises a tubular external component 21 having a cylindrical hole, two internal components 22 that can be slid longitudinally and rotated in unloaded condition in the hole, and nuts 23 screwed onto threaded segments 29 of each internal component. Nuts 23 and the threaded segment 29 on each internal component 22 constitute a means for loading or stressing the connection device. The external component 21 has two through openings 24 and 25 designed as slots, which openings are positioned transversely to its longitudinal axis and approximately at right angles to each other. The slots permit angular swinging adjustment of the rods within an angular divergence of, for example, 80°. The internal components have, in turn, cylindrical through openings 24' and 25', which together with the slots in the external component form through openings 24 and 25, in each of which a carbon filament rod on the one hand and an entrenchment screw on the other hand can be inserted. The rod and screw are not specifically shown in FIG. 2.

At their ends 22" at which through openings 24', 25' are located, each internal component 22 according to the invention has a recess 26 extending from openings 24', 25' to the ends 22". When nuts 23 are screwed tight, the axial pressure created by the component 22 pressing against the structural element or rod in through openings 24, 25 causes a flexible radial spread of the recess 26, thereby pressing of the ends 22" of the internal components against the inside of the external component 21. An external tooth 22' on the circumference of the internal component 22 fits into an internal indentation 21' in the external component 21, and through its positive connection considerably reinforces the rotation stability of a rod such as 13 clamped to a screw 12. The axis of the internal component 22, the transverse through opening 24', 25', and its recess 26, lie in one plane. Theoretically, the slot-shaped recesses 26 running -from the openings 24', 25' could be positioned at a specific angle, for example 30°, to said plane. However, its width must be less than the diameter of the opening or the inserted rod.

When two rods 12 and 13 are loaded, the connection device 20 is further advantageous when the resulting torques, with simultaneous tightening of nuts 23, cancel each other out, and thereby exert no undesired forces on the screw, and hence on the bone, upon stress or relaxation.

Figure 3:
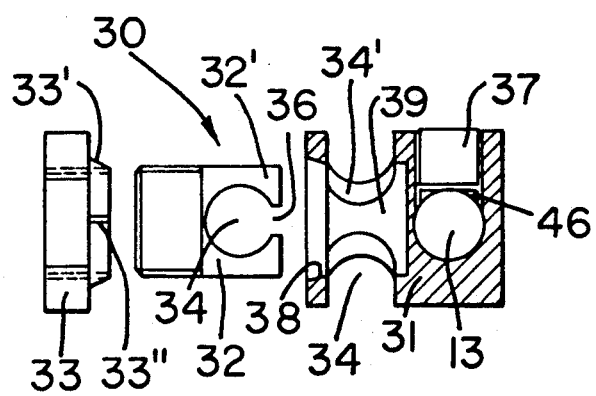
FIG. 3 is an exploded schematic view, partly in vertical section of a variant of the device of FIG. 2.

Referring to FIG. 3, a similar connection device 30 is shown. According to FIG. 3, an external component 31, has on one side an internal cylindrical component 32 and a nut 33 that can be screwed onto component 32. Internal component 32 can be inserted into a hole 39 of an external component 31, and together they form a transverse through opening 34, into which a rod can be inserted. As internal component 32 is slid axially into component 31, it is radially deformed by means of a recess 36 at its end 32', and it is thereby pressed firmly against external component 31.

The external component 31 also has a slot 34' which forms a through opening, by means of which the rods can be adjusted relative to one another at an angular divergence of 40°. A rod 13 is inserted into an opening 46 in external component 31, which opening is positioned at an angle of approximately 90° to the slot. The rod 13 is locked by a set screw 37.

The nut 33 is provided with a conical lug 33', corresponding to an internal cone 38 of external component 31, through which lug 33' an additional clamping effect is created, thereby practically eliminating the danger of an automatic loosening of the nut 33. Locking between the internal and the external components 32, 31, is increased by means of a longitudinal slot 33" in the conical lug 33'. Upon loading the conical lug 33' is pressed into the threading of internal component 32.

Figure 4:
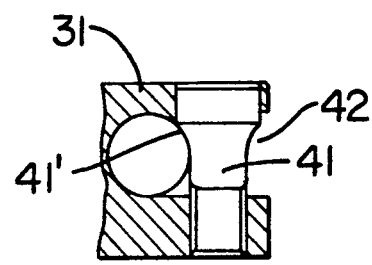
FIG. 4 is a fragmentary view partly in vertical section of another variant similar to that of FIG. 3.

In the connection device according to FIG. 4, only one segment of the corresponding external component 31 of FIG. 3 is shown. Instead of set screw 37, this component has a screw 41, positioned next to rod 13, which screw has a gripping surface 41', rounded off to correspond to rod 13, by means of which surface 41' the rod 13 is gripped when the screw is tightened. An end recess 42 increases the gripping effect.

Figure 5:
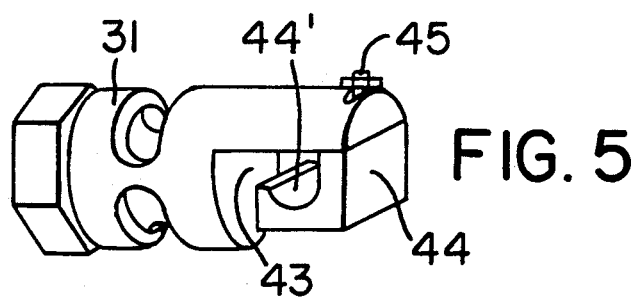
FIG. 5 is a perspective view of still another embodiment of the invention.

The connection device according to FIG. 5 differs from that of FIG. 3 only in the way one of the rods is held and loaded. External component 31 has at one end a segment-shaped recess 43' with a gripping flange 44 having a semi-circular recess 44', which is positioned adjustably by means of a screw 45. A rod can be placed in recess 44' of gripping flange 44, and is gripped by a turning of screw 45 between it and external component 31.

Figure 6:
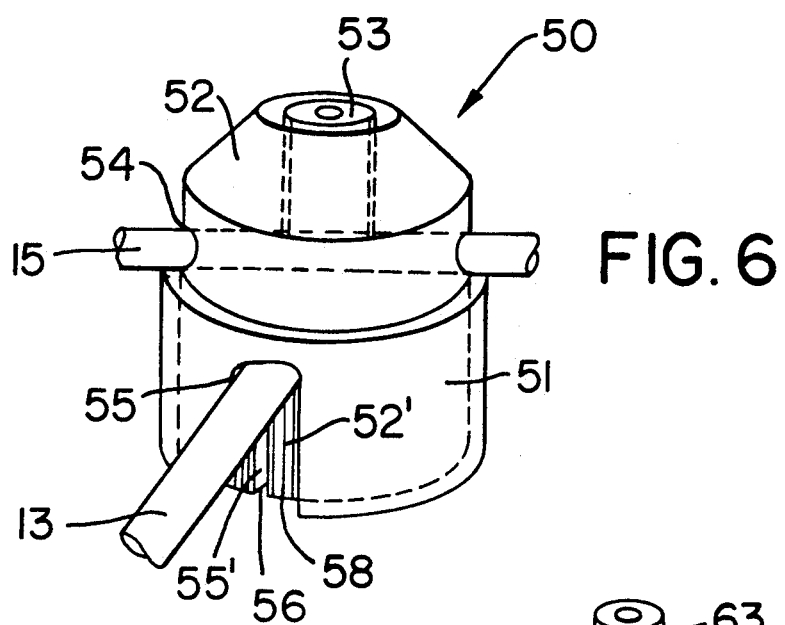
FIG. 6 is a perspective view of a further embodiment of the invention.

The connection device 50 shown in FIG. 6 consists of an essentially cylindrical internal component 52, a set screw 53 positioned coaxially in the component 52, and an external component 51, formed as a ring that encloses the internal component 52. Internal component 52 has a transverse through opening 54 for a rod 15, and a through opening 55 below and at right angles to the rod 15, into which a rod 13 can be slipped. Both sides of the external component 51 contacts a rod, either -rod 13 or rod 15. Where screw 53 is tightened, it presses on rod 15, which in turn presses on adjacent external component 51 and then on lower rod 13, which lies in internal component 52. In this way both rod 13 and rod 15 can be gripped simultaneously by the action of one and the same screw 53. Rod 15 lies on the top surface of component 51, while bottom rod 13 is located in a recess of external component 51 that opens downwardly.

According to the invention, internal component 52 has a recess 56, designed as a longitudinal slot, which starts from through opening 55 and extends to end 52' of internal component 52. When rods 13 and 15 are loaded and component 51 presses on lower rod 13 and subsequently on internal component 52, the additional pressure is created by the spreading of component 52. Matching denticulations 58 on components 52 and 51 increase the rotational rigidity.

This connection device 50 is particularly appropriate for connecting rods 15, 16 with rods 13, 14 as shown in FIG. 1, since in normal cases the latter are connected initially with Schanze screws 12 and only later are the connecting rods 15, 16 fixed.

Figure 7:
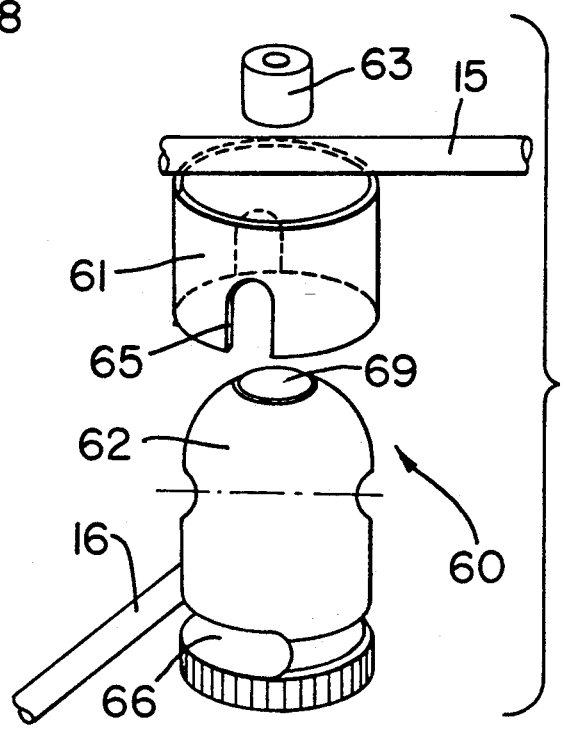
FIG. 7 is an exploded perspective view of still a further embodiment of the invention.

Referring to FIG. 7, the embodiment shown there differs from the device shown in FIG. 6 only in that instead of the longitudinal slot 56 (FIG. 6), the internal component has a transverse recess.

Specifically, the connection device 60 of FIG. 7 has an internal component 62 and an external component 61. The external component has a slot 65 in its lower part, extending in the axial direction. External component 61 is cylindrical and fits over the internal component 62. Internal component 62 has a transverse opening 62a for receiving a structural element 15 shown as a rod. At its upper end, internal component 62 has a threaded hole 69 for receiving a set screw 63. At its lower end, internal component 62 has a transverse slot 66 for receiving a second structural element, the rod 16.

The device 60 may be assembled by placing rod 16 in slot 66 and external component 61 over the internal component 62 so that slot 65 fits over rod 16. Rod 15 may then be inserted through opening 62a. When set screw 63 is advanced to load the device, rod 15 is forced against external component 61 causing it to press against rod 16. Rod 16 in turn presses component 62 causing a flexible bending of the lower portion of component 62, enhancing its engagement with external component 61. Recess 66 is designed in such manner that a rod such as the rod 16 inserted into it can be adjusted by a specific angle in relation to the upper rod 15, thereby permitting movement through the sector of a circle. A nut screwed onto an external threading of the internal component can be used instead of set screw 63.

Instead of inserting rod 16 into recess 66, and then placing the external component 61 on the internal component, rod 16 can be pushed into the through opening 65, 66 through the two components 62 and 61 after they are assembled. Surface 67 of component 62 and the facing internal surface of component 61 can be structured, e.g. notched, roughened or knurled to facilitate a frictional binding of the components.

Figure 8:
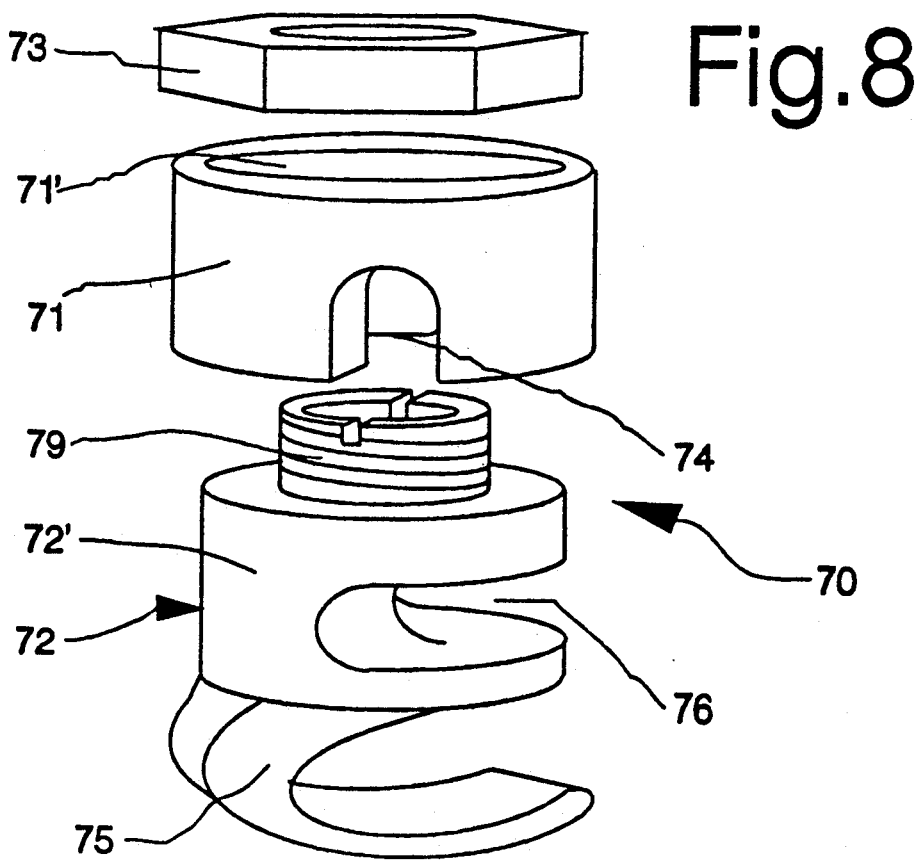
FIG. 8 is an exploded perspective view of another variant of the invention with a swivel hook.

The connection device 70 according to FIG. 8 has an internal component 72, composed of a threaded segment 79, a cylindrical segment 72' with a transverse slot 76, and a swivel-hook 75 forming the structural component. Here, again, an external component 71 having a cylindrical hole 71' is mounted on internal component 72. The external component 71 has a slot 74 in a generally axial direction. When assembled, the slots 74, 76 form a through hole for a structural element such as a rod 13 (FIG. 1). The rod inserted in the through hole is retained by a nut 73 that can be screwed on the threaded segment 79 of internal component 72. The rod 13 resting in recess 76 of internal component 72, creates a bending force and thus a radial deformation in the flexible area of internal component 72. In addition to the gripping of a structural component in internal component 72, which gripping areas through static friction, the two components additionally are bonded to each other by means of the said deformation and increase the mutual bonding of the structural elements, as already described. The transverse recess 76 of internal component 72, which simultaneously functions as through opening for a structural component, can also be designed in such manner that the rod inserted therein can move through a sector of a circle.

Figure 9:
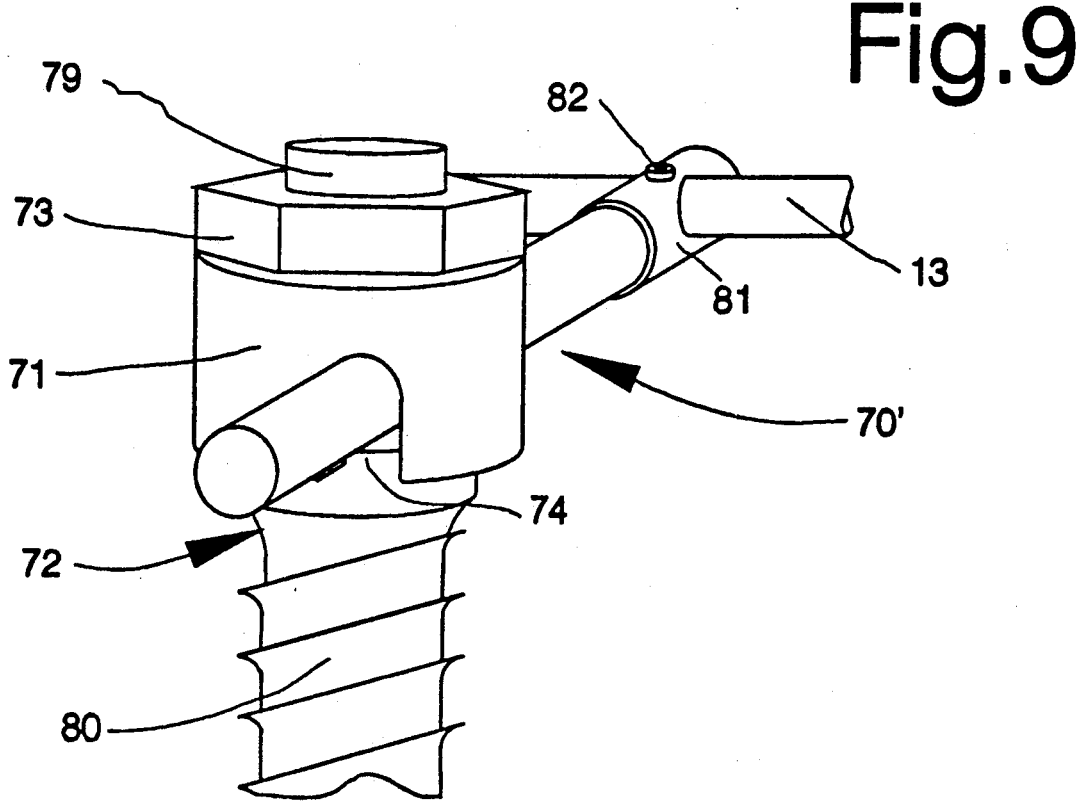
FIG. 9 is a perspective view of a further embodiment of the invention with a pedicle screw, assembled in a fixation system.

FIG. 9 shows a connection device 70', which differs from that of FIG. 8 only in having a pedicle screw 80, which is positioned as a structural component on internal cylindrical component 82. Otherwise, its components are identical with those of FIG. 8, and are therefore not described in detail. The structural component seated in the through hole formed by slots 74 and 76 is designed as cross-rod 81, having a transverse hole in which the actual connection rod 13 is held. A set screw 82 in cross-rod 81 serves as a retainer for the two rods.

Figure 10:
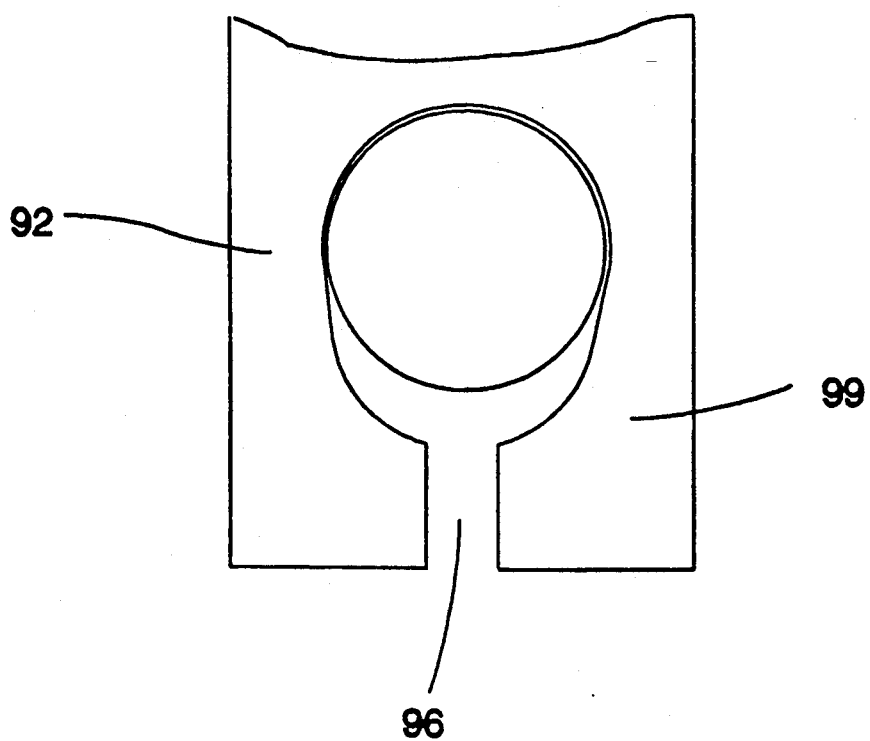
FIG. 10 is a schematic view of an internal component of a connection device according to the invention.

FIG. 10 shows an internal component 92 with a recess 96, which has a double hole 99 as through opening for a structural component. This double hole 99 is formed of two offset holes, with the offset hole positioned toward the end of internal component 92 having a diameter smaller than that of the other offset hole or the structural component, so that the spread can be increased.

Figure 11:
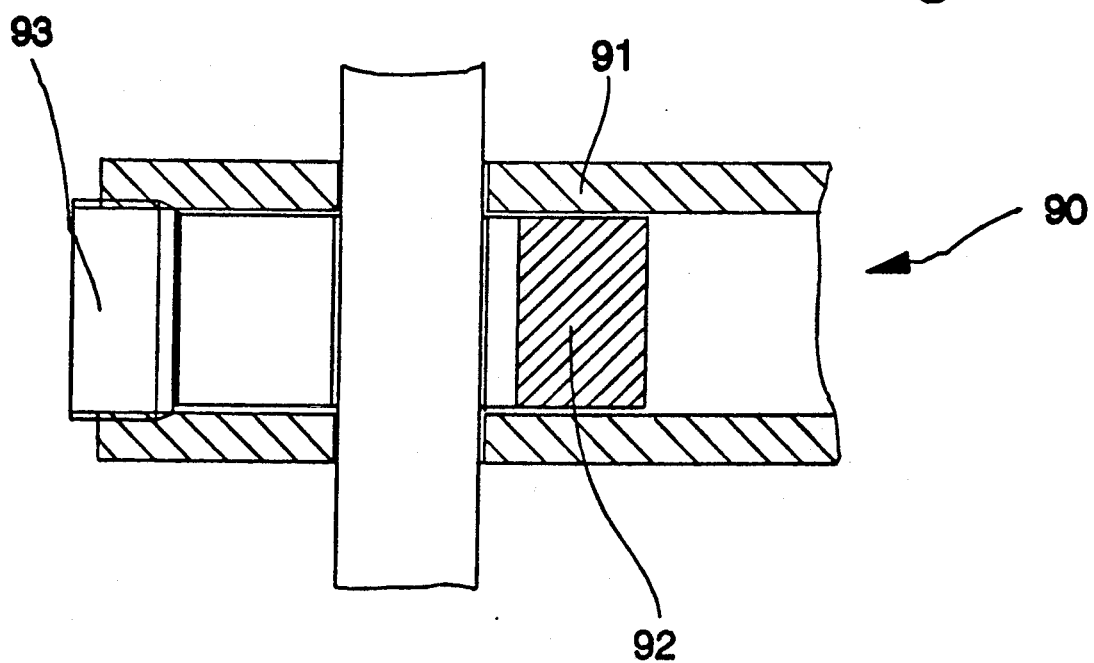
FIG. 11 is a fragmentary view in side elevation and partly in vertical section of a further variant.

The connection device 90 according to FIG. 11 differs from that of FIG. 2 only in that the loading means, instead of the nut, comprises a set screw 93, which can be screwed into external component 91, and which presses against internal component 92.

Needless to say, the invention can be embodied in a variety of other specific structures.

What is claimed is:

1. A connection device for the adjustable connection of a first support rod with either a bone screw or a second support rod in a surgical fixation system, said connection device comprising:
   (a) an external component having a cylindrical hole with a central axis;
   (b) a cylindrical internal component having a central axis adapted to be slidingly positioned in said cylindrical hole with its central axis aligned with the central axis of said hole, said internal component having a first slot and at least one through opening, said through opening being transverse to said central axis of said internal component and the central axis of said hole for receiving said support rod or bone screw; and
   (c) loading means for loading said connection device by causing relative sliding motion of said components;

whereby said support rod or bone screw can be locked in place, when inserted in said through opening, by means of the loading means causing the components to slide axially in relation to each other and the flexible deformation of said internal component through its first slot occurring when said internal component is slid against the inserted support rod or bone screw by said loading means and thereby pressed against the external component.

2. A connection device according to claim 1, wherein the internal component, when not pressed against the external component by the loading means, can slide longitudinally and rotate within the external component.

3. A connection device according to claim 1 wherein said internal component includes a threaded segment and said loading means includes a nut adapted to be screwed onto the threaded segment, thereby urging said internal component into contact with the external component.

4. A connection device according to claim 1, wherein the through opening of said internal component is in the form of a hole.

5. A connection device according to claim 1, wherein a through opening of said internal component is a second slot.

6. A connection device according to claim 1, wherein a through opening of said internal component permits angular swinging of a support rod or bone screw inserted therein.

7. A connection device according to claim 1, wherein the internal component includes an end having a first slot, said first slot of said internal component extends from its transverse through opening to its end, whereby pressing of said internal component against a support rod or bone screw inserted into its through opening creates a radial expansion of the slotted end of the internal component within the cylindrical hole of said external component.

8. A connection device according to claim 7, wherein two identical internal components having first slots are inserted within an external component.

9. A connection device according to claim 8, wherein the external component has two slotted through openings arranged perpendicularly in relation to one another for connecting a first support rod positioned approximately normal to a bone screw or second support rod.

10. A connection device according to claim 9, wherein the external component includes an end having a slot, said slot of the external component extends axially along said end facing the first slot of the internal component.

11. A connection device according to claim 1, wherein the internal component has a first slot running transverse to its longitudinal axis, which said first slot also forms a through opening for receiving a support rod or bone screw, whereby said first slot and support rod or bone screw inserted therein create a radial bending of the internal component upon loading.

12. A connection device according to claim 1, wherein the loading means comprises a set screw screwed into the external component, which set screw comes into contact with the internal component.

13. A connection device for the adjustable connection of a first support rod with either a bone screw or a second support rod in a surgical fixation system, said connection device comprising:
   (a) an external component having a cylindrical hole;
   (b) a cylindrical internal component, said internal component being adapted to be slidingly positioned on said cylindrical hole;
   (c) the internal and external components having roughened surfaces in contact with one another, when said inner component is positioned in said hole, said surfaces enhancing frictional contact between said components;
   (d) said internal component having a first slot and at least one through opening, said through opening being transverse to the axis of said internal component, for receiving said support rod or bone screw; and
   (e) loading means for loading said connection device by causing relative sliding motion of said components;

whereby said support rod or bone screw can be locked in place, when inserted in said through opening, by means of the loading means causing the components to slide axially in relation to each other and the flexible deformation of said internal component through its first slot occurring when said internal component is slid against the inserted support rod or bone screw by said loading means and thereby pressed against the external component.

14. A connection device according to claim 13 and comprising a plurality of grooves and ridges on the contacting surfaces of the internal and external components for positively connecting said components with one another.

15. A connection device according to claim 13, and comprising a plurality of grooves and ridges on the contacting surfaces of the internal and external components for substantially positively connecting said components with one another in the direction of rotation when said internal component is not pressed against the external component by the loading means.

16. A connection device for the adjustable connection of a first support rod with either a bone screw or a second support rod in a surgical fixation system, said connection device comprising:
   (a) an external component having a cylindrical hole and an internal cone;
   (b) an internal component adapted to be slidingly positioned in said cylindrical hole;
   (c) said internal component having a threaded segment, a first slot and at least one through opening, said through opening being transverse to the axis of the internal component, for receiving a support rod or bone screw; and
   (d) loading means for loading said connection device by causing relative sliding motion of said components, said loading means comprising a nut for engaging said threaded segment of said internal component, thereby to urge said internal component into contact with the external component; said nut having a lug for engagement with the internal cone of said external component;

whereby said support rod or bone screw can be locked in place, when inserted in said through opening, by means of the loading means causing the components to slide axially in relation to each other and the flexible deformation of said internal component through its first slot occurring when said internal component is slid against the inserted support rod or bone screw by said loading means and thereby pressed against the external component.

17. A connection device according to claim 16, wherein said conical lug has at least one longitudinal slot for improving the structural connection between said internal and external components.

18. A connection device for the adjustable connection of a first support rod with either a bone screw or a second support rod in a surgical fixation system, said connection device comprising:
   (a) an external component having a cylindrical hole;
   (b) a cylindrical internal component adapted to be slidingly positioned in said cylindrical hole, said internal component having a first slot, a first through opening transverse to the axis of said central component for receiving a first support rod, a second through opening for receiving a bone screw or second support rod;
   (c) loading means comprising a threaded axial hole and a set screw adapted to be seated in said threaded axial hole, to bear upon a first support rod in said first through opening and to urge said first support rod against said external component thereby to urge said external component against the bone screw or second support rod in said second through opening whereby said support rods or bone screw can be locked in place, when inserted in said through openings, by means of the loading means causing the components to slide axially in relation to each other and the flexible deformation of said internal component through its first slot occurring when said internal component is slid against the inserted support rod or bone screw by said loading means and thereby pressed against the external component.

19. A connection device for the adjustable connection of a first support rod with either a bone screw or a second support rod in a surgical fixation system, said connection device comprising:
(a) an external component having a cylindrical hole;
(b) a cylindrical internal component adapted to be axially slidingly positioned in said cylindrical hole, said internal component having a first slot and a first through opening transverse to the axis of said internal component for receiving a bone screw or second support rod and a second through opening for receiving a first support rod; and
(c) loading means comprising a threaded axial hole in said internal component and a set screw adapted to be seated in said threaded axial hole, to bear upon the bone screw or second support rod in said first through opening, and to urge said bone screw or second support rod against said external component, thereby to urge said external component against the first support rod in said second through opening;

whereby said support rods or bone screw can be locked in place, when inserted in said through openings, by means of the loading means causing the components to slide axially in relation to each other and the flexible deformation of said internal component through its first slot occurring when said internal component is slid against the inserted support rod or bone screw by said loading means and thereby pressed against the external component.

20. A connection device for the adjustable connection of a first support rod with either a bone screw or a second support rod in a surgical fixation system, said connection device comprising:
(a) an external component having a cylindrical hole;
(b) a cylindrical internal component adapted to be slidingly positioned in said cylindrical hole, said internal component having a threaded segment, a cylindrical segment with a transverse through slot for receiving a support rod and a swivel hook or pedicle screw, and
(c) loading means comprising a nut engaging the threaded segment of said internal component to bear upon said external component urging said external component against a support rod inserted into said recess whereby said support rod or bone screw can be locked in place, when inserted in said through slot, by mans of the loading means causing the components to slide axially in relation to each other and the flexible deformation of said internal component through its slot occurring when said internal component is slid against the inserted support rod or bone screw by said loading means and thereby pressed against the external component.

21. A connection device for the adjustable connection of a first support rod with either a bone screw or a second support rod in a surgical fixation system, said connection device comprising:
(a) an external component having a cylindrical hole;
(b) a cylindrical internal component adapted to be axially slidingly positioned in said external component, said internal component having an end, a slot at said end and a double hole through opening comprising first and second holes offset in relation to one another, said first hole, positioned toward said end of said internal equipment, having a smaller diameter than the second hole, or any support rod or bone screw to be inserted; and
(c) loading means for loading said connection device by causing relative sliding motion of said components whereby said support rod or bone screw can be locked in place, when inserted in said through opening, by means of the loading means causing the components to slide axially in relation to each other and the flexible deformation of said internal component through its slot occurring when said internal component is slid against the inserted support rod or bone screw by said loading means and thereby pressed against the external component.

* * * * *

UNITED STATES PATENT AND TRADEMARK OFFICE
CERTIFICATE OF CORRECTION

PATENT NO. : 5,312,402
DATED : May 17, 1994
INVENTOR(S) : Johannes Schlapfer and Martin Hess It is certified that error appears in the above-identified patent and that said Letters Patent is hereby corrected as shown below:

Col. 5, line 48,      cancel "areas" and substitute --arises--.

Col. 10, line 7,      cancel "mans" and substitute --means--.

Signed and Sealed this

Twenty-seventh Day of September, 1994

Attest:

BRUCE LEHMAN

*Attesting Officer*      *Commissioner of Patents and Trademarks*